United States Patent
Biedermann

[11] Patent Number: 5,825,499
[45] Date of Patent: Oct. 20, 1998

[54] METHOD FOR CHECKING WAFERS HAVING A LACQUER LAYER FOR FAULTS

[75] Inventor: Ernst Biedermann, Regensburg, Germany

[73] Assignee: Siemens Aktiengesellschaft, Munich, Germany

[21] Appl. No.: 740,253

[22] Filed: Oct. 25, 1996

[30] Foreign Application Priority Data

Oct. 25, 1995 [DE] Germany .................. 195 39 735.5

[51] Int. Cl.⁶ .......................... G01B 11/00; G01N 11/00; G01N 21/00

[52] U.S. Cl. .................... 356/394; 356/237; 250/559.46

[58] Field of Search .................... 356/394, 237, 356/239; 382/147, 149; 250/559.08, 559.46

[56] References Cited

U.S. PATENT DOCUMENTS

| | | | |
|---|---|---|---|
| 3,909,602 | 9/1975 | Micka | 356/394 |
| 4,628,531 | 12/1986 | Okamoto et al. | 356/237 |
| 4,633,504 | 12/1986 | Wihl | 356/237 |
| 4,954,723 | 9/1990 | Takahashi et al. | 336/237 |
| 4,975,972 | 12/1990 | Bose et al. . | |
| 5,506,793 | 4/1996 | Straayer et al. | 382/147 |

FOREIGN PATENT DOCUMENTS

| | | |
|---|---|---|
| 39 19 330 A1 | 12/1989 | Germany . |
| 4123916 A1 | 1/1992 | Germany . |
| 4324800 A1 | 2/1995 | Germany . |
| 4410603 C1 | 6/1995 | Germany . |
| 195 00 382 A1 | 7/1995 | Germany . |
| 44 13 831 A1 | 10/1995 | Germany . |
| 44 13 832 A1 | 10/1995 | Germany . |
| 2 286 670 | 8/1995 | United Kingdom . |
| WO 92/07250 | 4/1992 | WIPO . |

*Primary Examiner*—Frank G. Font
*Assistant Examiner*—Amanda Merlino
*Attorney, Agent, or Firm*—Herbert L. Lerner; Laurence A. Greenberg

[57] ABSTRACT

A wafer with a lacquer layer applied to it is checked automatically by lighting the wafer directly, so that the lacquer layer reflects the light. Resultant reflectance values of the reflected light are ascertained and buffer-stored and compared with corresponding values for a comparison wafer. It is ascertained whether the wafer is OK or defective from the result of the comparison in accordance with at least one predetermined judgment criterion.

10 Claims, 4 Drawing Sheets

METHOD FOR CHECKING WAFERS HAVING A LACQUER LAYER FOR FAULTS

BACKGROUND OF THE INVENTION

1. Field of the Invention

The invention relates to a method for checking wafers that have a lacquer layer, and in particular a batch of such wafers.

A batch of wafers is known to be a plurality of wafers that are part of a single production batch. The wafers may be various types of disks or wafers, for instance wafers used to produce semiconductor components, such as integrated circuits or individual semiconductors, or disks used to produce a compact disk (CD, CD-ROM). The method is intended for checking the lacquer layer, and optionally structures beneath it as well, for faultlessness. If the wafers are used in making semiconductor components, then the method is necessary, and can be applied, after every process step, in which a resist, lacquer or varnish layer has been applied to the wafer (which is known to be the case multiple times in such a production process). Defective wafers should be detected so that they can either be precluded entirely from the further course of production, or so that they can be suitably reprocessed before further production continues, and then on the condition of being fault-free (for which checking the reprocessed wafers is again a prerequisite), they can be introduced back into the normal course of production.

Such checks of wafers for faultlessness (for instance, checking for freedom of particles or in other words freedom from dirt and deposits, checking for a uniformly thick lacquer layer or for flaws in the lacquer layer) are known to be eminently important if good yields in the production process are to be attained.

Until now, such checks have been made manually, either with the aid of microscopes or without a microscope through the use of oblique light. On one hand, that is very tedious to the worker, especially to his or her eyes and back (due to poor posture caused by sitting for hours at a time). On the other hand, however, it also involves major uncertainties, because over time the ability of the worker to concentrate on detecting defects and sorting out good and bad wafers declines.

2. Summary of the Invention

It is accordingly an object of the invention to provide a method for checking wafers, which overcomes the hereinaforementioned disadvantages of the heretofore-known methods of this general type, which is as error-free as possible and which is able to lessen the burden on the worker in terms of health.

In German Published, Non-Prosecuted Patent Application DE 44 13 831 A1, corresponding to U.S. application Ser. No. 08/425,827, filed Apr. 20, 1995, a method is described by which wafers with a lacquer layer, that are used to produce integrated semiconductor memories and which have at least a first layer with structures, can be checked automatically. That application also describes apparatuses with which that method can be performed. Those apparatuses, as well as the apparatuses of German Published, Non-Prosecuted Patent Application DE 44 13 832 A1, corresponding to U.S. application Ser. No. 08/425,824, filed Apr. 20, 1995, are also suitable for performing the method of the present invention. The disclosure of those two earlier patent applications is thus hereby incorporated by reference in the present application, even though for the sake of easier comprehension of the method of the invention there will be some repetition below.

With the foregoing and other objects in view there is provided, in accordance with the invention, a method for automatically checking wafers having a lacquer layer, which comprises a) directly eluminating a wafer having a lacquer layer reflecting light; b) ascertaining a reflectance value of the reflected light by pixels for a plurality of points on a surface of the wafer with a picture-taking device disposed at a predetermined angle above the wafer for detecting pictures to be taken by pixels, and buffer-storing the reflectance value with an evaluation device connected to the picture-taking device; c) comparing the ascertained and buffer-stored reflectance values with predetermined comparison values; d) ascertaining whether the wafer is OK or defective from a result of the comparison between the ascertained and buffer-stored reflectance values and the comparison values, in accordance with at least one predetermined judgment criterion; and e) separating a wafer having been found defective from wafers having been found defect-free, if a plurality of wafers are being checked.

In accordance with another mode of the invention, there is provided a method which comprises indirectly lighting the wafer; placing the picture-taking device at a further angle, differing from the predetermined angle, relative to the surface of the wafer; and carrying out steps b) through e).

In accordance with a further mode of the invention, there is provided a method which comprises checking with indirect lighting and with the camera disposed at the further angle, only those disks having been found OK in the checking with direct lighting and with the camera disposed at the predetermined angle.

In accordance with an added mode of the invention, there is provided a method which comprises basing the comparison values on a given alignment of a comparison wafer used in ascertaining the comparison values, and aligning the wafer to be checked in accordance with the given alignment.

In accordance with an additional mode of the invention, there is provided a method which comprises basing the comparison values on a given alignment of a comparison wafer used in ascertaining the comparison values, and compensating for a different alignment of the wafer to be checked by a corresponding coordinate transformation of the pixels having reflectance values to be picked up.

In accordance with yet another mode of the invention, there is provided a method which comprises determining a first judgment criterion as a predetermined minimum amount of agreement between a particular ascertained, buffer-stored value of the reflectance and the comparison value associated with it.

In accordance with yet a further mode of the invention, there is provided a method which comprises determining a second judgment criterion by ascertaining a location of points on the wafer having pixels exceeding the judgment criterion, in the event that the first judgment criterion shows that the wafer is defective; ascertaining which of the points form coherent regions on the wafer from a location of the points; and determining that the wafer is OK in the event that the number of coherent regions is below a predetermined maximum amount.

In accordance with yet an added mode of the invention, there is provided a method which comprises determining a further second judgment criterion by ascertaining a location of points on the wafer having pixels exceeding the judgment criterion, in the event that the first judgment criterion shows that the wafer is defective; ascertaining which of the points form the coherent regions on the wafer from the location of the points; and determining that the wafer is OK, in the event that a size of the coherent regions is below a predetermined maximum amount.

In accordance with yet an additional mode of the invention, there is provided a method which comprises determining a third judgment criterion by judging a wafer found to be OK in accordance with one of the two second judgment criteria as defective overall, if a total number of the coherent regions and a total surface area occupied by the coherent regions on the wafer exceeds a predetermined proportion of a total area of the wafer.

In accordance with again another mode of the invention, there is provided a method which comprises determining a fourth judgment criterion by judging a wafer found to be OK in accordance with one of the two second judgment criteria as defective overall if a straight line can be run through it as an imaginary measuring line in at least one of the coherent regions, and if a number of points along at least one section of the measuring line having a reflectance value exceeding the first judgment criterion is greater than a predetermined maximum value, as referred along the respective section of the measuring line to the total number of points with values of reflectance having been ascertained.

In accordance with again a further mode of the invention, there is provided a method which comprises determining a fifth judgment criterion in the event that a wafer is determined to be OK in accordance with one of the second, third and fourth judgment criteria, by determining that the wafer is defective if points in a limit region of a coherent region have reflectance values differing by at least a factor of 10 from reflectance values resulting for points located outside the coherent region and other coherent regions in a further limit region around the coherent region.

In accordance with a concomitant mode of the invention, there is provided a method which comprises judging whether the wafer is OK or defective outside a portion of the wafer having structured units, with more stringent criteria than within the portion.

Other features which are considered as characteristic for the invention are set forth in the appended claims.

Although the invention is illustrated and described herein as embodied in a method for checking wafers, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
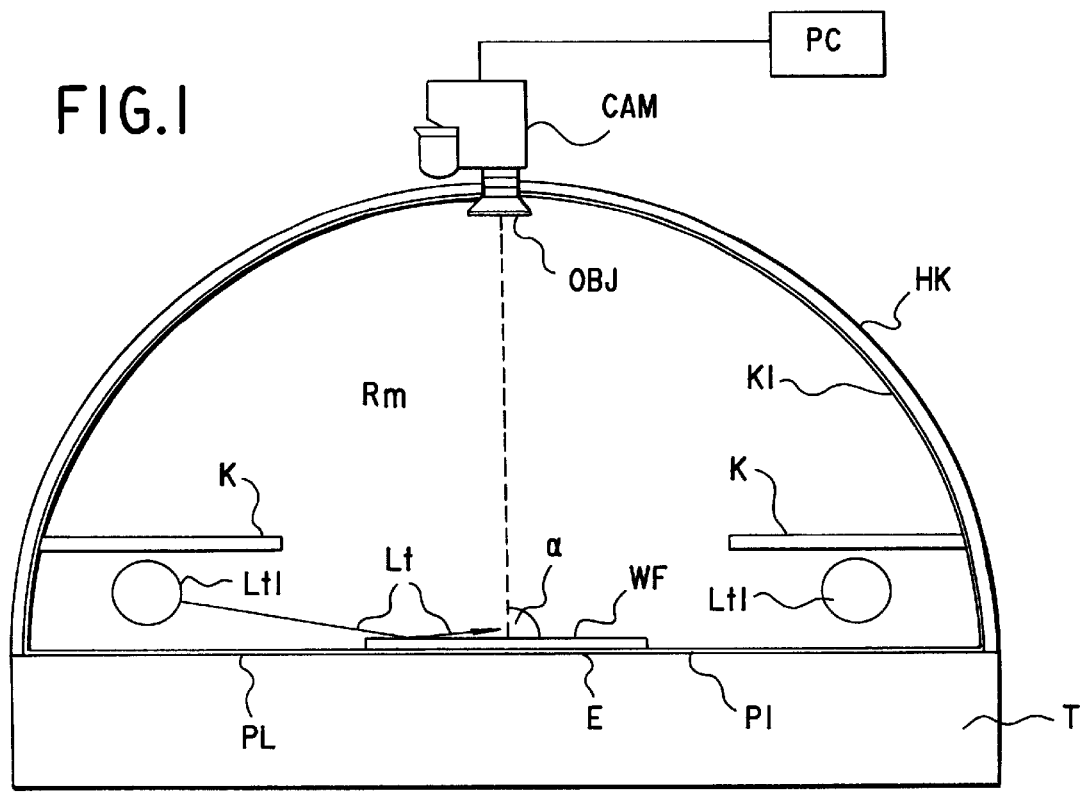
FIGS. 1–3 are diagrammatic, vertical-sectional views of advantageous embodiments of apparatuses that make the method possible.
Figure 2:
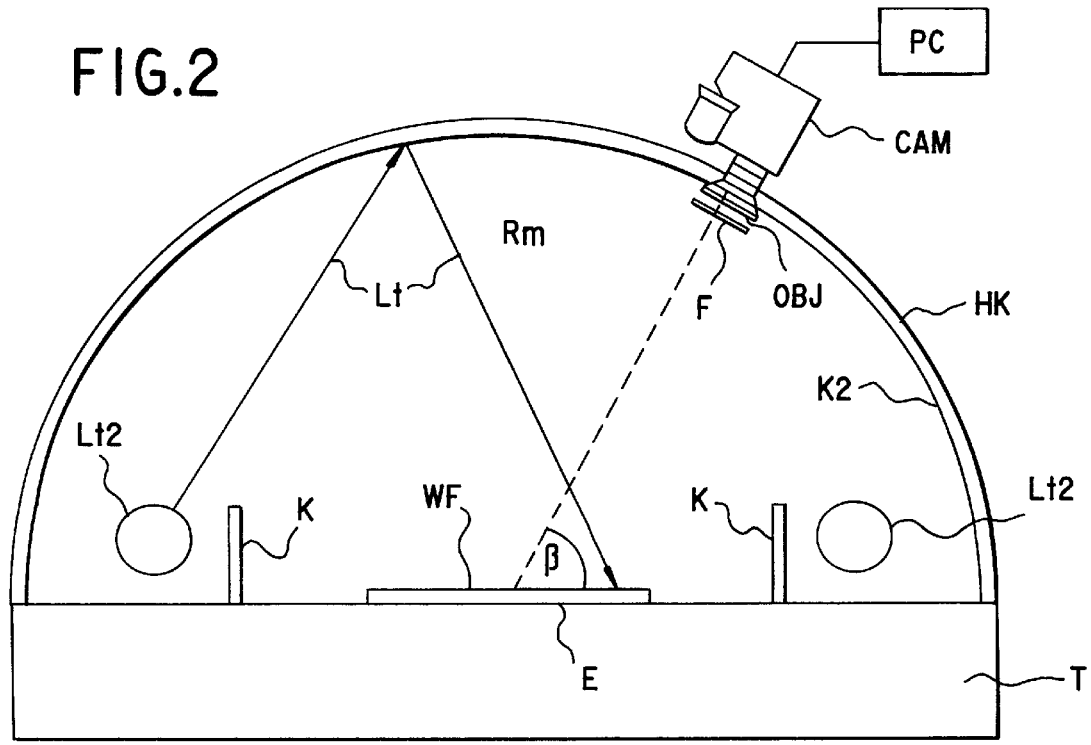
Figure 3:
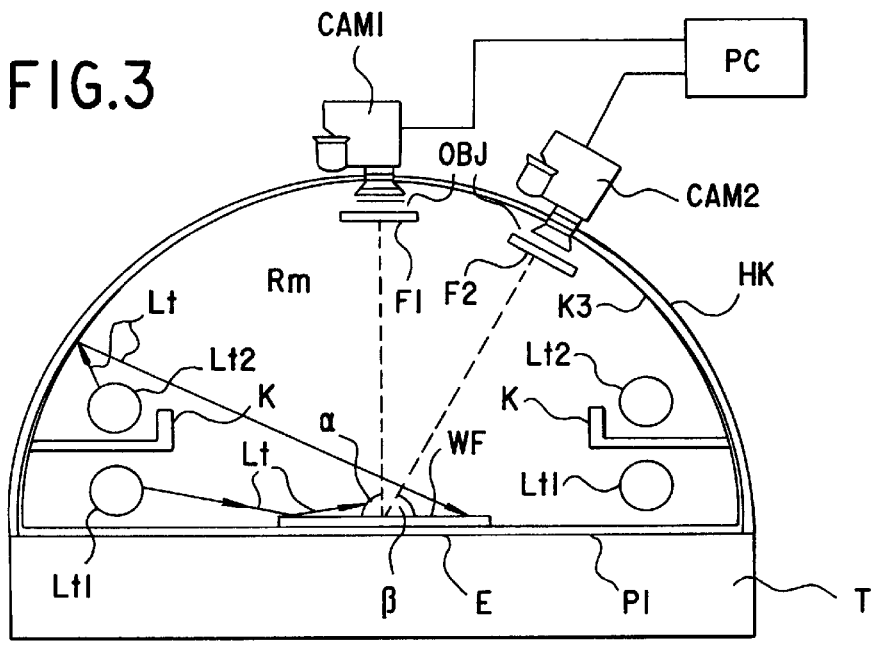

Before the method of the invention is described in further detail, a first one of the apparatuses suitable for the method will be briefly explained first:

Referring now to the figures of the drawings in detail and first, particularly, to FIG. 1 thereof, there is seen an apparatus that, by way of example, can be disposed on a table T or some other suitable, stable support surface (which also applies to the other two apparatuses of FIGS. 2 and 3). The apparatus has an element E for holding a wafer or disk WF to be checked, as well as a bottom plate Pl. However, the bottom plate Pl is not absolutely necessary. The element E may be a component of the bottom plate Pl. However, in accordance with other features of the apparatus, it may also be disposed on the bottom plate Pl or let into it. The apparatus also has a hemispherical cover device HK, with which the bottom plate Pl forms a largely closed interior chamber Rm. The cover device HK has a surface K1 which is optionally black, is disposed in the interior Rm and largely absorbs incident light Lt.

A preferably but not necessarily annular lighting device Lt1 which is disposed within this interior Rm provides direct lighting of the wafer WF to be checked. The annular structure enables uniform lighting of the wafer WF. As mentioned above, the hemispherical cover device HK has the surface K1, inside the sealed chamber Rm, that absorbs the incident light Lt.

A further cover device K, which does not admit incident light Lt and as much as possible absorbs it, is disposed above the lighting device Lt1. The further cover device K is constructed in such a way that the wafer WF is directly lightable through the use of the lighting device Lt1, while the hemispherical cover HK is for the most part covered relative to the direct light of the lighting device Lt1. As a consequence of these demands, it is favorable, especially with an annular construction of the lighting device Lt1, for the further cover device K to be constructed annularly as well.

Figure 4:
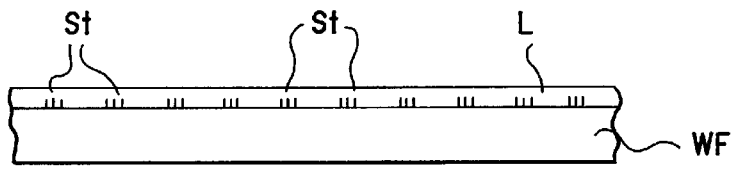
FIGS. 4 and 5 are respective cross-sectional and plan views of a wafer.
Figure 5:
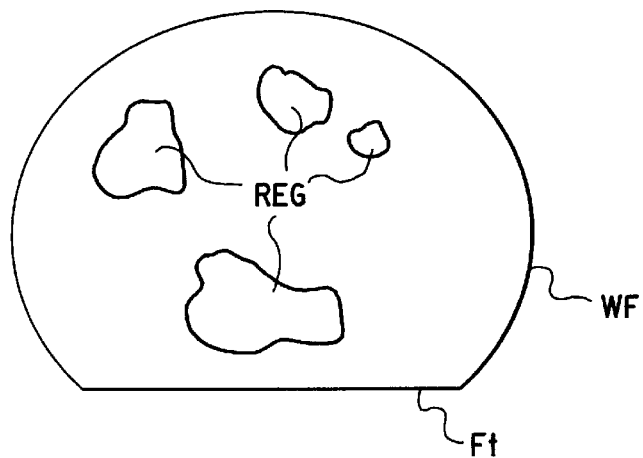
Figure 6:
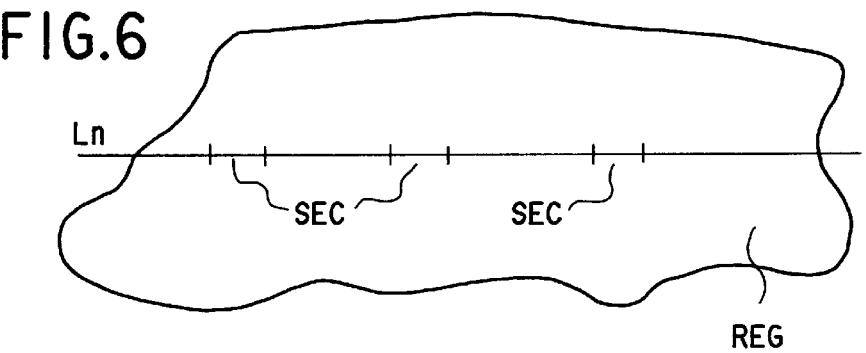
FIGS. 6 and 7 are enlarged, fragmentary, plan views of coherent regions on the wafer.
Figure 7:
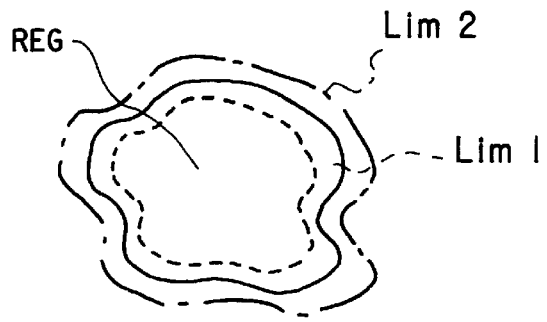
Figure 9:
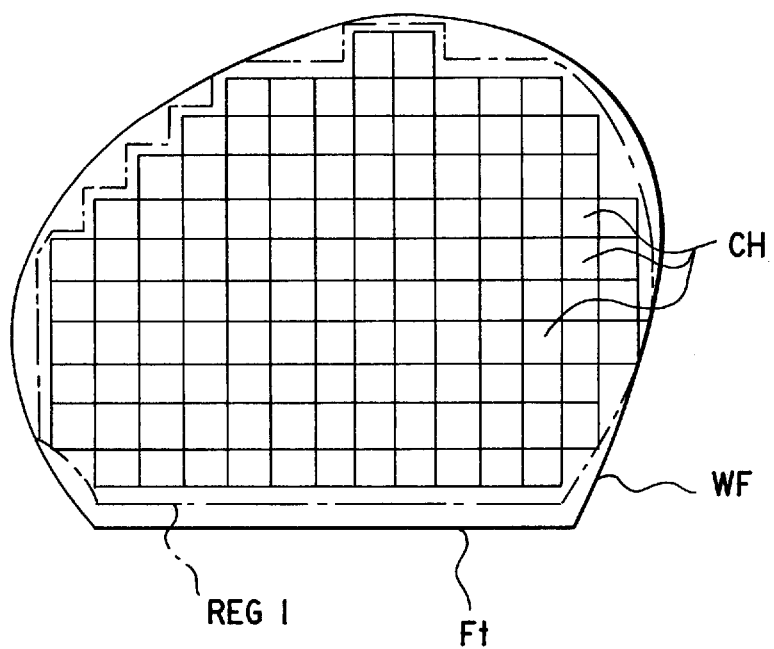
FIG. 9 is a view similar to FIG. 5 showing structured units of a portion of a wafer.

A picture-taking device CAM, typically a camera, is disposed at a given angle α from the element E for holding the wafer WF to be checked (and thus from the wafer WF that is to be checked itself), which is preferably a right angle. The picture-taking device CAM is disposed on the hemispherical cover device HK in such a way that its lens Obj points into the interior Rm and particularly is aimed at a location where the wafer WF to be checked is located during operation. The picture-taking device CAM may be disposed in such a way that its lens Obj points into the interior Rm, as is shown in FIG. 1, or in such a way that an edge of its lens Obj is approximately flush with the hemispherical cover HK. The picture-taking device CAM is intended to take pictures dotwise of the light Lt reflected by a resist, lacquer or varnish layer L shown in FIG. 4, for producing an image of the wafer WF to be checked.

The picture-taking device CAM is connected to an evaluation device PC, which serves to control the picture-taking device CAM and also serves to receive, buffer-store, process and output data ("pictures") transmitted by the picture-taking device CAM. These data may be transmitted in analog or digital fashion, as long as the picture-taking device CAM is already equipped for digital transmission (for instance if it has A/D converters). The evaluation device PC is typically a computer device, such as a personal computer or a data processing system. However, it is also conceivable that it be constructed solely of hardware which controls the method to be described below.

The following features of the device, among others, are possible and favorable:

The surface K1 of the hemispherical cover HK that absorbs the light Lt is black.

The light Lt projected by the lighting device Lt1 is white.

The further cover device K has a black surface.

The surface of the bottom plate Pl facing toward the hemispherical cover device HK is black.

If other parts of the picture-taking device CAM are located in the interior Rm, then they are disposed in such a way that, when observed from the wafer WF to be checked, they are concealed by the lens Obj.

The method described below in conjunction with FIGS. 4–9 can be carried out through the use of this apparatus and optionally its further features. It is suitable both for checking individual wafers WF and for checking from a plurality of wafers WF to all of the wafers WF in one batch of wafers WF (that is, wafers WF that are part of one common production batch).

Reflectance values of a light reflected correspondingly from another wafer (comparison wafer) are used as comparison values in the checking. The comparison wafer is identical to the wafer WF to be checked, with respect to its stage of production and its type. The resist, lacquer or varnish and optionally structures in the comparison disk located beneath the resist, lacquer or varnish, have already been found beforehand to be OK.

Usually, wafers WF have an orientation characteristic (in semiconductor wafers, these are already existing structures St of the wafer WF resulting from the current process step in the course of production), and/or usually a so-called flat Ft (that is, a region of the semiconductor wafer which is intrinsically round as seen in plan view, is flattened). In the exemplary embodiment of the method described below, it is assumed that the wafers WF to be checked have either such a flat Ft (see FIG. 5) or some other orientation characteristic such as structures St (see FIG. 4). However, the method functions even if the wafer WF to be checked has no orientation characteristic, since in that case, as seen from above, the wafer WF is uniform. In other words, the image of the wafer WF in the picture-taking device CAM is identical at every pixel, if the wafer WF is OK.

One essential characteristic of the method of the invention is that the checking proceeds automatically, or in other words without the intervention of human activities. On one hand, this protects the health of the worker (see the disadvantages of the prior art discussed at the outset above). On the other hand, however, it promotes the accuracy of the check, for the following reasons:

- more measurement points can be checked, that is the check is more accurate, for the same or even shorter measuring time (per wafer);
- human mistakes (transposing the detection of pass/fail and sorting in accordance with pass/fail) are precluded; and
- the throughput or in other words the productivity per worker increases for a shorter measuring time per wafer.

Moreover, the method of the invention also affords the opportunity for one worker to simultaneously operate several apparatuses that perform the method of the invention (for instance, putting the wafers in place and removing them, if not automated and starting the method, if not automated) and/or to check them, so that productivity can be increased even further (it is well known that higher productivity means lower production costs, which is eminently important nowadays to wafer manufacturers).

The method of the invention is carried out as follows (with respect to the apparatus, see FIGS. 1 and 3):

The wafer WF to be checked is lighted directly through the use of the lighting device Lt1, so that the lacquer layer L reflects the incident light Lt. The picture-taking device CAM (or CAM 1 in FIG. 3) takes a picture of the wafer WF in dots. The brightness of each image point or pixel of the picture-taking device CAM represents a reflectance value R of the reflected light Lt that results at a point on the surface of the lacquer L corresponding to the pixel (and thus on a point of the wafer WF) on the basis of the condition of the wafer WF.

At least a plurality of the thus-ascertained reflectance values R are transmitted by the picture-taking device CAM to the evaluation device PC connected to it and are buffer-stored.

Figure 8:
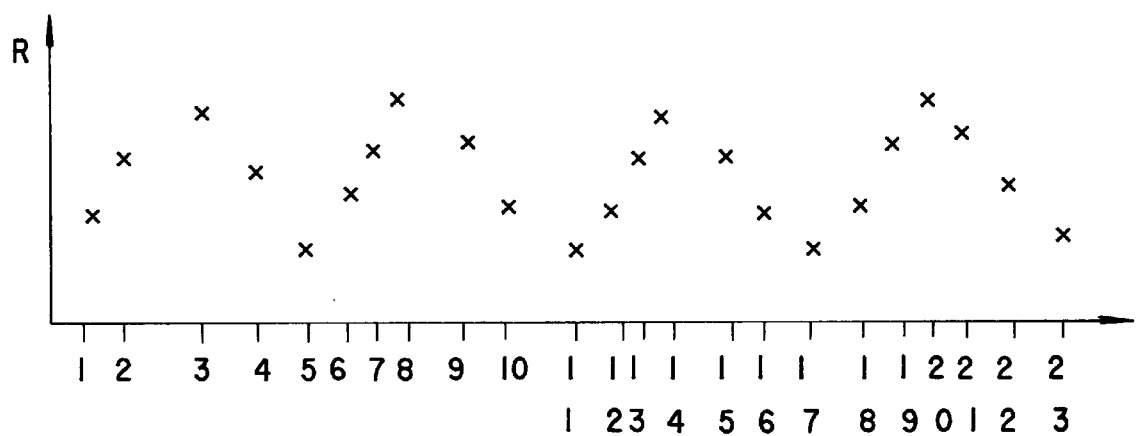
FIG. 8 is a diagram of a course of reflected light.

In the case of the reflectance value R, the course shown in FIG. 8, for instance, results (which need not necessarily be a kind of sine-wave curve). The abscissa corresponds to a geometrical association of the pixels to points on the wafer WF (such as coordinates). The particular reflectance value R can be read off on the ordinate.

The thus-ascertained and buffer-stored reflectance values R are each compared with one of the predetermined comparison values, which of course derive from a comparison wafer and are likewise stored in memory in the evaluation device PC. The results of these comparisons are subjected to at least one predetermined judgment criterion, from which it is ascertained whether the checked wafer WF will be classified as "OK" or as defective.

When a plurality of wafers WF, that is a batch of wafers WF, is checked, then following the check, the defective wafers are separated from the faultless wafers and are either discarded or reprocessed.

In particular, the determination as to whether the checked semiconductor wafer WF is OK or not is judged in accordance with at least one of the following judgment criteria:

A further judgment criterion is the amount of agreement (or non-agreement) that the particular ascertained, buffer-stored reflectance values R have with a particular associated comparison value. Although in practice the various values and comparison values never match exactly, nevertheless a maximally great agreement is to be sought. In this sense, a tolerance value (which is as small as possible) should be provided.

A second judgment criterion can be appended to the first judgment criterion, according to a further feature of the invention:

If the check in accordance with the first judgment criterion (initially) shows that the wafer WF is defective, then the location of those points on the wafer WF having associated pixels which exceed the first judgment criterion is ascertained. From this, information is then derived as to what points form coherent regions Reg on the wafer WF (typically, defects affect a plurality of points and not merely a single point, because of the surface area they require).

This second judgment criterion means that the number and/or the size of such coherent regions Reg may not exceed a predetermined maximum amount. If this maximum amount is exceeded, then the wafer WF is still found to be defective. Otherwise, it is found to be OK.

According to a third judgment criterion, a wafer WF which has been found OK in accordance with at least one of the two second judgment criteria, is nevertheless classified as defective if the total area SQ that all of the coherent regions Reg of the wafer WF to be checked have, exceeds a predetermined proportion of the total area of the wafer WF.

In accordance with a fourth judgment criterion (see FIG. 6), a wafer WF that has been found OK by at least one of the two second judgment criteria is nevertheless classified as defective, if in at least one of these coherent regions Reg, a straight line can be laid through it as an imaginary measuring line Ln, which is conceptually divided into sections Sec, and if along at least one of these sections Sec, the number of points having reflectance values R which exceed the first judgment criterion is greater than a given maximum value which, along the particular section Sec of this measuring line Ln, is referred to the total number of points the reflectance values R of which have been buffer-stored.

A practical check is made as to whether or not the reflectance values R for neighboring points, one of which meets the first judgment criterion and the other does not, change abruptly. This fifth judgment criterion is employed for wafers WF that meet the above-described second through fourth judgment criteria, or in other words when they have been found good in accordance with those judgment criteria.

In a limit region Lim1 of a coherent region Reg in such a wafer WF, that is a boundary to wafer regions outside the region Reg, a check is performed as to whether or not the reflectance values R ascertained from points of this limit region Lim1 differ by a factor of at least 10 from such reflectance values R that have been ascertained with respect to points which are located in a further limit region Lim2 outside the region Reg. If so, then the wafer is found defective.

If wafers WF, in a portion Reg1, have structured units CH (such as semiconductor chips of a semiconductor wafer, in which case so-called peripheral regions exist in which a chip can no longer be accommodated completely for space reasons, noting that at present those peripheral regions are usually left free of chips), it has proved to be advantageous if more-stringent limit values are employed, for the limit values used in the above-described judgment criteria, in that part of the wafer WF which is located outside the region Reg1 with the structured units CH, with respect to a decision "Defect: Yes or no?", than for those limit regions that pertain to points of the portion Reg1.

According to a further feature of the invention, it is advantageous if following the above-described method, either every wafer WF or every wafer WF thus far found to be good is subjected to the method once again, under the following two varied conditions:

The wafer is lighted indirectly (see FIGS. 2 and 3) and the picture-taking device CAM or CAM2 is disposed at a further angle β from the surface of the wafer WF that is other than the angle α. The point of this repeated check under altered conditions is to find defects that cannot be seen with direct lighting and/or at the picture-taking angle α, but can be found under suitably modified conditions.

This configuration, which corresponds to FIGS. 2 and 3, is described at length in the aforementioned U.S. applications and German Published, Non-Prosecuted Patent Applications, to which reference is expressly made for the sake of the disclosure (however, it should be noted that the angle α used therein corresponds to the angle β of FIGS. 2 and 3 of the present invention, and that the angle designated herein as "α" is shown and described in the aforementioned applications as a right angle ("perpendicular") with respect to FIGS. 1 and 2).

In one case (that will generally be the more frequent one), in which the comparison wafer has undergone a certain alignment (orientation) in the ascertainment of the comparison values (for instance, alignment with the flat Ft of a semiconductor wafer), it is favorable to align the wafer WF to be checked accordingly as well, because then the reflectance values R can be compared directly with one another without any special coordinate conversion (with respect to the orientation of the wafer WF).

However, according to the invention it is also possible, in the case where the wafer WF is aligned differently from the comparison wafer or is not aligned at all, to rearrange the reflectance values of the wafer WF to be checked (or those of the comparison wafer) through the use of a corresponding coordinate transformation that corrects the different alignment, in such a way that in terms of position they correspond to the alignment of the comparison wafer (or of the wafer WF to be checked).

I claim:

1. A method for automatically checking wafers having a lacquer layer, which comprises:
   a) directly illuminating a wafer having a lacquer layer reflecting light;
   b) ascertaining a reflectance value of the reflected light by pixels simultaneously for a plurality of points on a surface of the wafer with a picture-taking device disposed at a given angle above the wafer for detecting pictures to be taken by pixels, and buffer-storing the reflectance value with an evaluation device connected to the picture-taking device;
   c) comparing the ascertained and buffer-stored reflectance values with reflectance comparison values of a comparison wafer;
   d) ascertaining whether the wafer is OK or defective from a result of the comparison between the ascertained and buffer-stored reflectance values and the comparison values, in accordance with at least two predetermined judgment criteria, including:
      determining a first judgment criterion as a predetermined minimum amount of agreement between particular ascertained, buffer-stored reflectance values and the comparison values associated with them; and
      determining a second judgment criterion as follows:
         ascertaining a location of points on the wafer having pixels exceeding the first judgment criterion, in the event that the first judgment criterion shows that the wafer is defective;
         ascertaining which of the points form coherent regions on the wafer from the location of the points; and
         determining that the wafer is OK in the event that the number of the coherent regions is below a predetermined maximum amount; and
   e) separating the wafer having been found defective from wafers having been found defect-free, if a plurality of wafers are being checked.

2. The method according to claim 1, wherein the given angle is a first angle and the method further comprises:
   indirectly lighting the wafer;
   placing the picture-taking device at a second angle, differing from the first angle, relative to the surface of the wafer; and
   carrying out steps b) through e).

3. The method according to claim 2, which comprises checking with indirect lighting and with the picture-taking device disposed at the second angle, only those disks having been found OK in the checking with direct lighting and with the picture-taking device disposed at the first angle.

4. The method according to claim 1, which comprises basing the comparison values on a given alignment of a comparison wafer used in ascertaining the comparison values, and aligning the wafer to be checked in accordance with the given alignment.

5. The method according to claim 1, which comprises basing the comparison values on a given alignment of a comparison wafer used in ascertaining the comparison values, and compensating for a different alignment of the wafer to be checked by a corresponding coordinate transformation of the pixels having reflectance values to be picked up.

6. The method according to claim 1, which comprises determining a further second judgment criterion as follows:

ascertaining a location of points on the wafer having pixels exceeding the first judgment criterion, in the event that the first judgment criterion shows that the wafer is defective;

ascertaining which of the points form the coherent regions on the wafer from the location of the points; and determining that the wafer is OK, in the event that a size of the coherent regions is below a predetermined maximum amount.

7. The method according to claim 6, which comprises determining a third judgment criterion as follows:

judging a wafer found to be OK in accordance with one of the two second judgment criteria as defective overall, if a total surface area occupied by the coherent regions on the wafer of the total number of the coherent regions exceeds a predetermined proportion of a total area of the wafer.

8. The method according to claim 6, which comprises determining a third judgment criterion as follows:

judging a wafer found to be OK in accordance with one of the two second judgment criteria as defective overall if a straight line can be run through it as an imaginary measuring line in at least one of the coherent regions, and if a number of points along at least one section of the measuring line having a reflectance value exceeding the first judgment criterion is greater than a predetermined maximum value, referred along the respective section of the measuring line to the total number of points with values of reflectance having been ascertained.

9. The method according to claim 8, which comprises determining a fourth judgment criterion as follows:

in the event that a wafer is determined to be OK in accordance with one of the second or third judgment criteria, determining that the wafer is defective if points in a limit region of a coherent region have reflectance values differing by at least a factor of 10 from reflectance values resulting for points located outside the coherent region and other coherent regions in a further limit region around the coherent region.

10. The method according to claim 1, which comprises judging whether the wafer is OK or defective outside a portion of the wafer having structured units, with more stringent criteria than within the portion.

* * * * *